United States Patent [19]

Hamprecht et al.

[11] 4,316,015
[45] Feb. 16, 1982

[54] 6H-1,2,4,6-THIATRIAZINE-1,1-DIOXIDES

[75] Inventors: Gerhard Hamprecht, Weinheim; Rolf-Dieter Acker, Leimen; Bruno Wuerzer, Otterstadt, all of Fed. Rep. of Germany

[73] Assignee: BASF Aktiengesellschaft, Fed. Rep. of Germany

[21] Appl. No.: 199,820

[22] Filed: Oct. 23, 1980

[30] Foreign Application Priority Data

Oct. 30, 1979 [DE] Fed. Rep. of Germany ....... 2943703

[51] Int. Cl.³ .......................................... C07D 285/00
[52] U.S. Cl. ........................................................ 544/7
[58] Field of Search ............................................ 544/7

[56] References Cited

U.S. PATENT DOCUMENTS 4,013,447  3/1977  Kay ..................................... 544/7

FOREIGN PATENT DOCUMENTS 1946262  3/1971  Fed. Rep. of Germany .
2026625 12/1971  Fed. Rep. of Germany .
2508832  9/1975  Fed. Rep. of Germany .

Primary Examiner—John M. Ford
Attorney, Agent, or Firm—Keil & Witherspoon

[57] ABSTRACT 6H-1,2,4,6-Thiatriazine-1,1-dioxides of the formula I

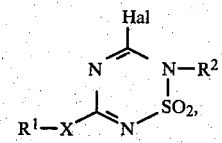

where $R^1$ is an aliphatic radical, a cycloaliphatic radical, a substituted aliphatic radical, a cycloalkoxy-substituted aliphatic radical, unsubstituted or substituted phenyl, or unsubstituted or substituted benzyl, $R^2$ is hydrogen, an aliphatic radical, a cycloaliphatic radical or substituted alkyl, X is oxygen, sulfur, sulfinyl or sulfonyl and Hal is halogen, herbicides containing these compounds, processes for their preparation, and methods for using the products as herbicides.

2 Claims, No Drawings

6H-1,2,4,6-THIATRIAZINE-1,1-DIOXIDES

The present invention relates to novel 6H-1,2,4,6-thiatriazine-1,1-dioxides, processes for the preparation of these compounds, herbicides which contain these compounds, and the use of the compounds as herbicides.

German Laid-Open Application DOS 1,946,262 discloses that substituted 6H-1,2,4,6-thiatriazin-5-one-1,1-dioxide derivatives are obtained when, for example, adducts of 2 moles of alkyl isocyanate and 1 mole of chlorosulfonyl isocyanate are reacted with alkyl alcohols, whilst German Laid-Open Application DOS No. 2,508,832 discloses their preparation by cyclizing N'-carboalkoxy-N-sulfamyl-guanidine under alkaline conditions. The herbicidal action of the compounds is also disclosed in the last-mentioned DOS.

We have found that 6H-5-halo-1,2,4,6-thiatriazine-1,1-dioxides of the general formula I

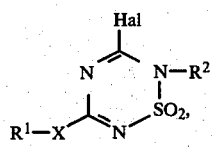

where
$R^1$ is a saturated or unsaturated straight-chain aliphatic alkyl, alkenyl or alkynyl radical of up to 10 carbon atoms, a cycloaliphatic radical of 3 to 7 carbon atoms, a branched, saturated or unsaturated aliphatic (alkyl, alkenyl, alkynyl) radical of 3 to 10 carbon atoms, a halogen-, alkoxy- or alkylmercapto-substituted straight-chain or branched aliphatic radical of 2 to 10 carbon atoms, a cycloalkoxy-substituted aliphatic radical of 4 to 10 carbon atoms, unsubstituted or halogen-, lower alkyl- or lower alkoxy-substituted phenyl, or unsubstituted or halogen-substituted benzyl, $R^2$ is hydrogen, a straight-chain aliphatic radical of 1 to 10 carbon atoms, a cycloaliphatic radical of 3 to 7 carbon atoms, a branched aliphatic radical of 3 to 10 carbon atoms or halogen- or alkoxy-substituted alkyl of 2 to 10 carbon atoms, X is oxygen, sulfur, sulfinyl or sulfonyl and
Hal is halogen,
possess a good herbicidal action and are valuable intermediates for the preparation of active ingredients for crop protection agents, and for the preparation of dyes and drugs.

Examples of $R^1$ and $R^2$ in the formula I are methyl, ethyl, propyl, isopropyl, cyclopropyl, butyl, isobutyl, sec.-butyl, tert.-butyl, 1-pentyl, cyclopentyl, hexyl, cyclohexyl, 3-pentyl, 1,2-dimethylpropyl, 1,3-dimethylbutyl, 2-chloroethyl, 2-chloropropyl, 3-chloropropyl, 2-chloroisopropyl, 1-chloromethylpropyl, 1-ethyl-2-methylpropyl, 1,2,2-trimethylpropyl, 1,2-dimethylhexyl, 1-cyclohexylethyl, 2-chlorobut-3-yl, 2-chloro-2-methylpropyl, 2-fluorobut-3-yl , 2-fluoro-2-methylpropyl, 2-fluoroisopropyl, tert.-amyl, chloro-tert.-butyl, 2,2,2-trifluoroethyl, methoxyethyl, ethoxyethyl, 3-methoxypropyl, methoxyisopropyl, 3-methoxybutyl, 1-methoxy-but-2-yl, ethoxy-tert.-butyl, methoxy-tert.-butyl, 2-methoxy-butyl and 4-methoxy-butyl.

Further examples of $R^1$ are allyl, methallyl, crotyl, 2-ethyl-hex-2-en-1-yl, hex-5-en-1-yl, 2-methyl-but-2-en-1-yl, 2-methyl-but-1-en-3-yl, but-1-yn-3-yl, but-2-yn-1-yl, but-1-en-3-yl, propargyl, 2-methyl-but-1-en-4-yl, 2-methyl-but-2-en-4-yl, 3-methyl-but-1-en-3-yl, methylmercaptoethyl, ethylmercapto-ethyl, 3-methylmercapto-propyl, 3-methylmercapto-butyl, 1-methylmercaptobut-2-yl, methylmercapto-tert.-butyl, 2-methylmercapto-butyl, cyclohexoxy-ethyl, benzyl, 2,6-dichlorobenzyl, 2-chloro-6-fluorobenzyl, 2,6-difluorobenzyl, phenyl, 4-chlorophenyl, 3,4-dichlorophenyl, 4-tert.-butylphenyl, 4-methoxy-3-chlorophenyl, 4-methoxyphenyl, 2-methylphenyl and 2-methyl-4-chlorophenyl.

Hal is fluorine, chlorine, bromine or iodine.

Further, we have found that the novel compounds are obtained in a simple manner if a compound of the general formula II

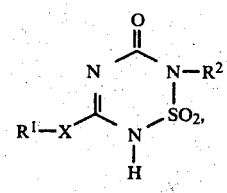

where $R^1$, $R^2$ and X have the above meanings, or an alkali metal salt or alkaline earth metal salt thereof, is reacted with an acid halide of phosphoric acid, phosphorous acid, carbonic acid, oxalic acid or sulfurous acid, in the presence or absence of a solvent or diluent and in the presence or absence of a reaction accelerator at from 0° to 160° C., under atmospheric or superatmospheric pressure, continuously or batchwise.

If 6-ethyl-3-methoxy-6H-1,2,4,6-thiatriazin-5-one-1,1-dioxide and phosgene are used as the starting materials, the course of the reaction can be represented by the following equation:

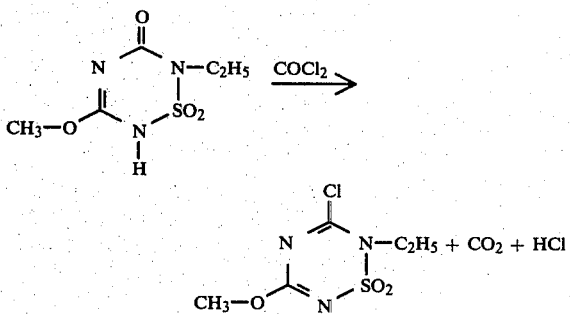

Advantageously, solvents or diluents which are inert under the reaction conditions are used for the reaction. Examples of suitable solvents are halohydrocarbons, especially chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, o-, m- and p-dichlorobenzene, o-, m- and p-dibromobenzene, o-, m- and p-chlorotoluene, and 1,2,4-trichlorobenzene, ethers, eg. ethyl propyl ether, methyl tert.-butyl ether, di-n-butyl ether, diisopropyl ether, anisole, dioxane and ethylene glycol dimethyl ether, nitrohydrocarbons, eg. nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane and 2,2,3-trimethylpentane, or esters, eg. ethyl acetate, and mixtures of the above. Other preferred solvents are inorganic acid chlorides, eg. phosphorus oxychloride, or mixtures of these with inert chlorohydrocarbons, eg. with 1,2-dichloroethane. The solvent is advantageously used in an amount of from 100 to 2,000 percent by weight, preferably from 200 to 700 percent by weight, based on the starting material of the formula II.

Preferred acid halides are thionyl chloride, sulfur tetrafluoride, phosgene, oxalyl chloride, phosphorus tribromide and especially phosphorus pentachloride, phosphorus trichloride and phosphorus oxychloride. The reaction is in general carried out with from 1.0 to 1.5, preferably from 1.05 to 1.2, moles of acid halide per mole of starting material II; in the case of the phosphorus pentahalide, from 0.7 to 1.5, preferably from 1.0 to 1.2, moles thereof are used per mole of starting material II.

Where a phosphorus (V) halide is used as the halogenating agent, it is advisable to use a phosphorus oxyhalide as the diluent, preferably in an amount of from 1 to 10 moles per mole of starting material II.

The phosphorus(V) halide can also be prepared directly in situ, for example by reacting a mixture of a phosphorus(III) halide in the phosphorus oxyhalide, or in one of the above inert solvents, with the requisite stoichiometric amount of active halogen, for example by the method described in U.S. Pat. No. 1,906,440, after which the starting material II is added and the main reaction is effected.

Advantageous reaction accelerators to use are an N-disubstituted linear or cyclic carboxylic acid amide, a tetraalkyl-substituted urea or a tertiary amine, preferably in amounts of from 1 to 10 percent by weight based on starting material II. Mixtures of the said catalysts may also be used for the reaction. Furthermore, salts of diamines, e.g. the diamine hydrochlorides, or quaternary salts of amines, may be used. Preferred catalysts are triethylamine, pyridine, N,N-dimethylaniline, N-ethylpiperidine, N-methylpyrrolidine, $\alpha$-, $\beta$-, or $\gamma$-picoline, quinoline, isoquinoline, quinazoline, quinoxaline, N-propyldiisopropylamine, 2,6- and 2,4-lutidine, N-(4-pyridyl)-pyridinium chloride hydrochloride, p-dimethylaminopyridine, pyrimidine, acridine, dimethylformamide, diethylformamide, N-methylformanilide, N,N-dimethylacetamide, N-methylpyrrolidone and tetramethylurea.

Some of the 6H-1,2,4,6-thiatriazin-5-one-1,1-dioxides required as starting material II are known; both these and the compounds not previously known can be prepared by reaction of N-carbo-alkoxy-O-alkyl-isoureas According to their spectroscopic data, the compounds have the structure shown in formula II. However, depending on the solvent, a certain proportion of the tautomeric form IIa may also be present and these compounds, being in equilibrium with the compounds II, also constitute suitable starting materials.

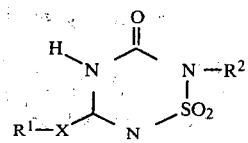

The process for the preparation of the novel compounds is advantageously carried out by introducing the starting material II, with or without one of the above inert diluents, into the reaction vessel, adding the halogenating agent at from 0° to 60° C., preferably from 20° to 40° C., and then heating the mixture so as to avoid a sudden, too high rate of evolution of gas.

However, it is also possible to add the starting material II, which may or may not be mixed with one of the above inert diluents, to the halogenating agent.

Where phosgene is used (whether starting material II is added to the halogenating agent or vice versa), it is advisable to add a reaction accelerator.

To complete the reaction, the mixture is then stirred for from 0.5 to 15 hours at from 0° to 160° C., preferably from 80° to 130° C. The degree of conversion can easily be followed by a spectroscopic method, for example by the shift in the proton resonance signals of the radicals $R^2$ or $R^1$.

The end product I is isolated from the reaction mixture in a conventional manner, for example by distilling off the solvent and the excess halogenating agent. This gives the desired end products in a pure form, though they may, if required, be purified further by recrystallization, chromatography or distillation.

The methods given below relate to the preparation of the starting compounds of the formula II.

METHOD 1

198 parts (the parts referred to being by weight) of methylaminosulfonyl chloride and 162 parts of triethylamine were introduced simultaneously, via 2 separate lines, into a stirred mixture of 202 parts of N-carbomethoxy-O-methylisourea in 1,570 parts of acetonitrile at 25°-30° C. After stirring for 3 hours at 25° C., the hydrochloride which had precipitated was filtered off and the filtrate was evaporated down under reduced pressure. The residue was dissolved in 1,500 parts of 1,2-dichloroethane and this solution was extracted once with water and twice with 0.5 N hydrochloric acid. After drying the organic solution over magnesium sulfate and evaporating it down under reduced pressure, 257 parts of N-carbomethoxy-N'-methylsulfamyl-O-methylurea, of $n_D^{25}=1.4851$, were obtained.

96 parts of this product were dissolved in 235 parts of absolutely dry methanol, 153.5 parts of sodium methylate (30% strength by weight) were added and the mixture was stirred under reflux for 3 hours. It was then evaporated down under reduced pressure, the residue was dissolved in water, and the aqueous solution was extracted once with ether and then acidified with dilute sulfuric acid. The product was filtered off, washed with water and dried, giving 68 parts (=82.5% of theory) of 6-methyl-3-methoxy-6H-1,2,4,6-thiatriazin-5-one-1,1-dioxide or melting point 198°-202° C.

METHOD 2

37.9 parts of isopropylaminosulfonyl chloride and 26.3 parts of triethylamine were added simultaneously, through two separate lines, to a stirred mixture of 54 parts of N-carbomethoxy-S-benzyl-isothiourea and 740 parts of 1,2-dichloroethane at 5°–10° C. After 4 hours' stirring at 25° C., the reaction mixture was extracted once with 200 parts of water and twice with 100 parts of 0.5 N hydrochloric acid at a time. It was then dried and evaporated down under reduced pressure, giving 79 parts of N-carbomethoxy-N'-isopropylsulfamyl-S-benzyl-isothiourea of $n_D^{25}=1.5598$. This product crystallized on trituration with hexane, the crystals having a melting point of 76°–78° C. 76 parts of N-carbomethoxy-N'-isopropylsulfamyl-S-benzylisothiourea were dissolved in a mixture of 44 parts of 50% strength by weight sodium hydroxide solution and 200 parts of water, and the solution was stirred for 5 minutes at 85° C. The reaction mixture was then cooled and acidified with 15% strength hydrochloric acid, and the oil which precipitated was taken up in methylene chloride. This solution was dried over magnesium sulfate, filtered over neutral alumina and evaporated down under reduced pressure, giving 59.5 parts of 6-isopropyl-3-benzylmercapto-6H-1,2,4,6-thiatriazin-5-one-1,1-dioxide (86.3% of theory), of melting point 124°–130° C.

METHOD 3

59.6 parts of cyclohexylaminosulfonyl chloride and 26.9 parts of pyridine were introduced, through two separate lines, into a stirred solution of 39.6 parts of N-carbomethoxy-O-methylisourea in 300 parts of ethyl acetate at 15°–20° C. After 4 hours' stirring at 25° C., the reaction mixture was extracted once with water and once with 0.5 N hydrochloric acid, dried and then evaporated down under reduced pressure. This gave 79 parts of N-carbomethoxy-N'-cyclohexylsulfamyl-O-methylisourea of $n_D^{25}=1.4970$. After trituration with a small amount of ether, the compound crystallized, and the crystals had a melting point of 84°–86° C. 15 parts of the N-carbomethoxy-N'-cyclohexylsulfamyl-O-methylisourea were dissolved in a mixture of 9 parts of 50% strength by weight sodium hydroxide solution and 20 parts of water and the solution was stirred for 4 minutes at 55°–60° C. It was then cooled, extracted once with ether, and stirred into a mixture of 9.5 parts of concentrated hydrochloric acid and 10 parts of water. The product was filtered off, washed with water and dried, giving 9 parts of 6-cyclohexyl-3-methoxy-6H-1,2,4,6-thiatriazin-5-one-1,1-dioxide, of melting point 173°–177° C.

METHOD 4

In the course of 25 minutes, 95 parts of isopropylaminosulfonyl chloride were stirred into a mixture of 96 parts of N-carbomethoxy-O-isopropylisourea and 73 parts of triethylamine in 700 parts of tetrahydrofuran at 10°–15° C. After then stirring for one hour at 25° C., the reaction mixture was extracted once with water and once with 0.5 N hydrochloric acid, dried and evaporated down under reduced pressure. This gave 130 parts of N-carbomethoxy-N'-isopropylsulfamyl-O-isopropyl-isourea, of melting point 62°–64° C. 33.7 parts of this product were cyclized with 17.6 parts of 50% strength by weight sodium hydroxide solution in 30 parts of water for 5 minutes at 55°–60° C. The mixture was extracted with ether and then acidified, and the product was filtered off, washed with water and dried, giving 22 parts of 6-isopropyl-3-isopropoxy-6H-1,2,4,6-thiatriazin-5-one,1,1-dioxide of melting point 164°–167° C.

METHOD 5

12 parts of 6-isopropyl-3-isopropoxy-6H-1,2,4,6-thiatriazin-5-one-1,1-dioxide were dissolved in a mixture of 10.4 parts of 30% strength by weight sodium methylate and 64 parts of methanol at 25° C. On evaporating down the mixture, 13.8 parts of 2-sodium-6-isopropyl-3-isopropoxy-6H-1,2,4,6-thiatriazin-5-one-1,1-dioxide, melting with decomposition at 123° C., were obtained.

METHOD 6

140 parts of N-carboxymethyl-N'-methylsulfamyl-O-methylurea in a mixture of 79.5 parts of sodium carbonate, 450 parts of water and 31 parts by volume of 2 N sodium hydroxide solution were stirred for 10 minutes at 45° C. The reaction mixture was cooled, extracted with ether and then slowly stirred into a mixture of 78 parts of concentrated sulfuric acid and 150 parts of ice water. The product was filtered off, washed with water and dried, giving 81 parts of 6-methyl-3-methoxy-6H-1,2,4,6-thiatriazin-5-one-1,1-dioxide (68% of theory), of melting point 195°–199° C.

The Examples which follow relate to the preparation of the novel compounds.

EXAMPLE 1

215 parts of 6-methyl-3-methoxy-6H-1,2,4,6-thiatriazin-5-one-1,1-dioxide were introduced into a stirred mixture of 275 parts of phosphorus pentachloride and 1,480 parts of phosphorus oxychloride at room temperature, and the mixture was heated to 110° C. in the course of 30 minutes. After 4 hours' stirring under reflux, the reaction mixture was evaporated down under reduced pressure, giving 235 parts (99.6% of theory) of 5-chloro-6-methyl-3-methoxy-6H-1,2,4,6-thiatriazine-1,1-dioxide, of melting point 77°–83° C. (Compound No. 1).

EXAMPLE 2

154 parts of phosphorus pentachloride were added, in the course of 2 minutes, to a stirred mixture of 128 parts of 6-ethyl-3-methoxy-6H-1,2,4,6-thiatriazin-5-one-1,1-dioxide and 840 parts of phosphorus oxychloride at 25° C. The reaction mixture was then stirred for 5½ hours under reflux, after which it was evaporated down under reduced pressure. The oil which remained was taken up in 300 parts of 1,2-dichloroethane and the solution was chromatographed over neutral alumina (Activity I). After evaporating down, 127.5 parts (91% of theory) of 5-chloro-6-ethyl-3-methoxy-6H-1,2,4,6-thiatriazine-1,1-dioxide, of melting point 63°–70° C., were obtained (Compound No. 2).

EXAMPLE 3

50 parts of phosphorus pentachloride were added to a stirred mixture of 41.4 parts of 6-methyl-3-ethoxy-6H-1,2,4,6-thiatriazin-5-one-1,1-dioxide, 100 parts of 1,2-dichloroethane and 100 parts of phosphorus oxychloride at room temperature. The reaction mixture was then stirred for 12 hours under reflux. After evaporating down under reduced pressure, 43.5 parts (96.5% of theory) of 5-chloro-6-methyl-3-ethoxy-6H-1,2,4,6-thiatriazine-1,1-dioxide, of melting point 75°–80° C., were obtained (Compound No. 3).

EXAMPLE 4

50 parts of phosphorus pentachloride were added to a stirred mixture of 44 parts of 6-n-propyl-3-methoxy-6H-1,2,4,6-thiatriazin-5-one-1,1-dioxide and 268 parts of phosphorus oxychloride at 22° C., and the batch was heated to 110° C. in the course of 20 minutes. After 7 hours' stirring under reflux, the reaction mixture was evaporated down under reduced pressure, giving 45 parts of oily 5-chloro-6-n-propyl-3-methoxy-6H-1,2,4,6-thiatriazine-1,1-dioxide; NMR: (CDCl$_3$) N-CH$_2$ 4.0–4.28δ.

Distillation at 125°–130° C./0.01 mbar gave 40.3 parts (84% of theory) of pure product (Compound No. 4).

EXAMPLE 5

Phosgene gas was passed for 14 hours into a stirred suspension of 25 parts of 6-ethyl-3-methylmercapto-6H-1,2,4,6-thiatriazin-5-one-1,1-dioxide in 2.5 parts of DMF and 245 parts of 1,2-dichloroethane at 83° C. After evaporating down under reduced pressure, 27 parts of a viscous oil were isolated; according to the NMR spectrum, this contained about 45% of 5-chloro-6-ethyl-3-methylmercapto-6H-1,2,4,6-thiatriazine-1,1-dioxide. A sample was distilled at 136°–144° C./0.01 mbar; NMR: (CDCl$_3$) N-CH$_2$ 4.04–4.42δ(q), CH$_3$S 2.52δ(s) (Compound No. 5).

Further Examples of novel compounds are given below, in Table 1.

TABLE 1

| Compound no. | R$^1$ | R$^2$ | X | M.P.[°C.] or $n_D^{25}$ |
|---|---|---|---|---|
| 6 | CH$_3$ | i-C$_3$H$_7$ | O | 1.5237 |
| 7 | CH$_3$ | sec-C$_4$H$_9$ | O | |
| 8 | CH$_3$ | i-C$_4$H$_9$ | O | |
| 9 | CH$_3$ | tert.-C$_4$H$_9$ | O | |
| 10 | CH$_3$ | ⟨H⟩ | O | 105–109 |
| 11 | CH$_3$ | CH$_2$—CH$_2$Cl | O | |
| 12 | CH$_3$ | CH$_2$—CH$_2$—O—CH$_3$ | O | |
| 13 | C$_2$H$_5$ | C$_2$H$_5$ | O | 1.5150 |
| 14 | C$_2$H$_5$ | n-C$_3$H$_7$ | O | 1.5100, B.p. 118/0.01 |
| 15 | C$_2$H$_5$ | i-C$_3$H$_7$ | O | 1.5201, B.p. 119–121/0.01 |
| 16 | C$_2$H$_5$ | n-C$_4$H$_9$ | O | |
| 17 | C$_2$H$_5$ | i-C$_4$H$_9$ | O | |
| 18 | C$_2$H$_5$ | sec-C$_4$H$_9$ | O | |
| 19 | C$_2$H$_5$ | tert.-C$_4$H$_9$ | O | |
| 20 | C$_2$H$_5$ | CH$_2$—CH$_2$Cl | O | |
| 21 | C$_2$H$_5$ | ⟨H⟩ | O | |
| 22 | n-C$_3$H$_7$ | CH$_3$ | O | 37–41 |
| 23 | n-C$_3$H$_7$ | C$_2$H$_5$ | O | |
| 24 | n-C$_3$H$_7$ | C$_2$H$_5$ | S | |
| 25 | n-C$_3$H$_7$ | n-C$_3$H$_7$ | O | |
| 26 | n-C$_3$H$_7$ | i-C$_3$H$_7$ | O | |
| 27 | n-C$_3$H$_7$ | sec-C$_4$H$_9$ | O | |
| 28 | n-C$_3$H$_7$ | tert.-C$_4$H$_9$ | O | |
| 29 | n-C$_3$H$_7$ | CH$_2$CH$_2$—O—CH$_3$ | O | |
| 30 | n-C$_3$H$_7$ | ⟨H⟩ | O | |
| 31 | i-C$_3$H$_7$ | CH$_3$ | O | viscous, NMR (CDCl$_3$) H—C—O 4.97–5.3∂ |
| 32 | i-C$_3$H$_7$ | C$_2$H$_5$ | O | |
| 33 | i-C$_3$H$_7$ | n-C$_3$H$_7$ | O | 1.5009 |
| 34 | i-C$_3$H$_7$ | i-C$_3$H$_7$ | O | viscous, NMR (CDCl$_3$) H—C 4.9–5.4∂, CH$_3$—C 1.35, 1.45, 1.62, 1.72∂ |
| 35 | i-C$_3$H$_7$ | sec.-C$_4$H$_9$ | O | |
| 36 | i-C$_3$H$_7$ | ⟨H⟩ | O | |
| 37 | n-C$_4$H$_9$ | CH$_3$ | O | |
| 38 | n-C$_4$H$_9$ | C$_2$H$_5$ | O | |
| 39 | n-C$_4$H$_9$ | n-C$_3$H$_7$ | O | |
| 40 | n-C$_4$H$_9$ | i-C$_3$H$_7$ | O | |
| 41 | n-C$_4$H$_9$ | sec.-C$_4$H$_9$ | O | |
| 42 | n-C$_4$H$_9$ | CH$_2$—CH$_2$Cl | O | |
| 43 | n-C$_4$H$_9$ | i-C$_3$H$_7$ | S | |
| 44 | i-C$_4$H$_9$ | CH$_3$ | O | |
| 45 | i-C$_4$H$_9$ | i-C$_3$H$_7$ | 0 | 1.5049 |
| Compound | R$^1$ | R$^2$ | X | M.p.[°C.] or $n^{25}$ |
| 46 | sec.-C$_4$H$_9$ | CH$_3$ | O | |

TABLE 1-continued

| No. | R¹ | R² | X | M.p. [°C] or n²⁵ |
|---|---|---|---|---|
| 47 | sec.-C₄H₉ | C₂H₅ | O | |
| 48 | sec.-C₄H₉ | i-C₃H₇ | O | viscous, NMR (CDCl₃) (CH₃)₂C 1.66, 1.77∂ |
| 49 | tert.-C₄H₉ | CH₃ | O | |
| 50 | tert.-C₄H₉ | C₂H₅ | O | |
| 51 | tert.-C₄H₉ | i-C₃H₇ | O | |
| 52 | ⬡–H | CH₃ | O | 45–53 |
| 53 | ⬡–H | C₂H₅ | O | |
| 54 | ⬡–H | i-C₃H₇ | O | |
| 55 | CH₂=CH—CH₂ | CH₃ | O | |
| 56 | CH₂=CH—CH₂ | C₂H₅ | O | |
| 57 | CH₂=CH—CH₂ | i-C₃H₇ | O | |
| 58 | C₆H₅—CH₂ | CH₃ | O | |
| 59 | C₆H₅—CH₂ | i-C₃H₇ | O | |
| 60 | Cl—⬡—CH₂ | CH₃ | O | |
| 61 | CH₃—O—CH₂—CH₂ | CH₃ | O | |
| 62 | CH₃—O—CH₂—CH₂ | C₂H₅ | O | |
| 63 | CH₃—S—CH₂—CH₂ | CH₃ | O | |
| 64 | CH₃—S—CH₂—CH₂ | i-C₃H₇ | O | |
| 65 | CH₃ | CH₃ | S | 103–107 |
| 66 | C₂H₅ | CH₃ | S | |
| 67 | n-C₃H₇ | CH₃ | S | |
| 68 | CH₃ | i-C₃H₇ | S | |
| 69 | CH₃ | n-C₃H₇ | S | |
| 70 | C₆H₅—CH₂ | CH₃ | S | viscous, NMR (CDCl₃) CH₃ 3.4∂, CH₂ 4.47∂ |
| 71 | Cl—⬡— | i-C₃H₇ | S | 146–148 |
| 72 | Cl—⬡— | CH₃ | S | 109 |

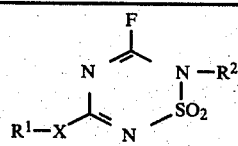

| Compound no. | R¹ | R² | X | M.p. [°C] or n²⁵ |
|---|---|---|---|---|
| 73 | CH₃ | CH₃ | O | viscous, NMR (d₆DMSO) O—CH₃ 3.9∂, N—CH₃ 3.1∂ |
| 74 | CH₃ | C₂H₅ | O | |
| 75 | C₂H₅ | CH₃ | O | |
| 76 | CH₃ | CH₃ | S | |
| 77 | C₂H₅ | CH₃ | S | |

The novel active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenzene, paraffins, e.g. petroleum fractions, alcohols, e.g. methanol and butanol, amines e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agents in general contain from 0.1 to 95% by weight of active ingredient, preferably from 0.5 to 90%.

Application rates depend on the weeds to be combated and their growth stages, and vary from 0.1 to 15, preferably from 0.2 to 5, kg of active ingredient per hectare. The higher rates are suitable for total elimination of plant growth.

The agents, and the ready-to-use preparations obtained therefrom, e.g., solutions, emulsions, suspensions, powders, dusts, pastes or granules, are applied in conventional manner, e.g. by spraying, atomizing, dusting, broadcasting, treating seed or watering. Examples of such formulations are as follows.

EXAMPLE I 90 parts of weight of compound 1 is mixed with 10 parts by weight of N-methyl-α-pyrrolidone. A mixture is obtained which is suitable for application in the form of very fine drops.

EXAMPLE II 10 parts by weight of compound 2 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE V 20 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE VI 5 parts by weight of compound 1 is intimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion.

EXAMPLE IX 20 parts of compound 1 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The new compounds may be applied in admixture with each other, with other herbicides, or with other crop protection agents, e.g., agents for combating pests or phytopathogenic fungi or bacteria. The compounds may also be mixed with mineral salt solutions used to remedy nutritional or trace element deficiencies.

The herbicidal action of the new compounds and their tolerance by certain crop plants is demonstrated in greenhouse experiments.

Experiment 1

Loam was filled into 10 liter plastic buckets and tubers of Cyperus esculentus were planted therein. Seeds of Cyperus iria were also sown. After a few days young rice plants having a stem length of about 10 cm were planted. The loam was kept muddy from the start, and after the rice plants had been planted they were flooded to a depth of 3 cm. The herbicidal active ingredients were then strewn or sprayed as uniformly as possible onto this miniature rice paddy. 5-Chloro-6-methyl-3-methoxy-6H-1,2,4,6-thiatriazine-1,1-dioxide, at rates of 1.0 and 2.0 kg/ha, suppressed Cyperaceae growth quite considerably. The rice plants were hardly damaged, if at all; what damage was caused was minor and temporary.

Experiment 2

The seeds of the test plants (cf. Table 1) were sown shallow, and separately, according to species, in a sandy loam in plastic flowerpots having a volume of 300 cm$^3$. For the preemergence treatment, the active ingredient were applied to the surface of the soil immediately after the seeds had been sown. The vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals, and prevented readily volatile substances from evaporating.

For the postemergence treatment, the plants were first grown in the vessels to a height of from 3 to 10 cm, depending on growth form, before being treated. No cover was placed on the vessels.

The pots were set up in the greenhouse—species from warmer areas at from 25° to 40° C., and species from moderate climates at 15° to 30° C. The experiments were run for from 3 to 5 weeks. During this period, the plants were tended and their reactions to the various treatments assessed. The following tables contain the compounds investigated, the application rates in kg/ha of active ingredient, and the plants used for the tests. The scale used for assessment was 0 to 100, 0 denoting no damage or normal emergence, and 100 denoting nonemergence or complete destruction of at least the visible plant parts.

The following tables demonstrate the selective herbicidal action of the compounds according to the invention on both pre- and postemergence application. A special application technique is to spray the active ingredients with the aid of spraying equipment in such a way that the leaves of sensitive crop plants are if possible not hit; the active ingredients reach the soil or unwanted plants growing below the crop plants (post-directed, lay-by treatment).

In view of the many application methods possible, the agents according to the invention, or mixtures containing them, may be used in addition to the crop plants listed in the tables in a larger number of other crops for eliminating unwanted growth.

The following crop plants are given by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |

| Botanical name | Common name |
|---|---|
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum bicolor (s. vulgare) | grain sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vivia faba | tick beans |
| Vigna sinensis (V. unguiculata) | cow peas |
| Vitus vinifera | grapes |
| Zea mays | Indian corn, sweet corn, maize |

TABLE 1

List of plant names

| Botanical name | Abbreviation in tables | Common name |
|---|---|---|
| Avena fatua | Avena fatua | wild oats |
| Centaurea cyanus | Centaurea cyan. | cornflower |
| Chenopodium spp. | Chenpod. spp. | lambsquarters |
| Cyperus esculentus | | yellow nutsedge |
| Cyperus iria | | rice flatsedge |
| Datura stramonium | Datura stramon. | jimsonweed |
| Eleocharis acicularis | | slender spikerush |
| Euphorbia geniculata | Euphorb. genic. | wild poinsettia |
| Matricaria chamomilla | Matric. cham. | wild chamomile |
| Oryza sativa | Oryza sativa | rice |
| Sida spinosa | Sida spinosa | teaweed |
| Solanum nigrum | Solan. nigr. | black nightshade |
| Zea mays | Zea mays | Indian corn |

TABLE 2

Selective herbicidal action; preemergence treatment in the greenhouse

| | | Test plants and % damage | | | | |
|---|---|---|---|---|---|---|
| Active ingredient | kg/ha | Oryza sativa | Zea mays | Centaurea cyan. | Sida spinosa | Solanum nigrum |
| No. 1 | 1.0 | 0 | 15 | 98 | 95 | 95 |
| | 1.0 | 55 | 32 | 50 | 50 | 50 |

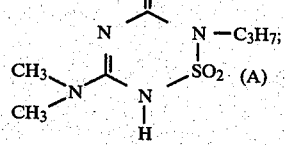

(A)

TABLE 2-continued

Selective herbicidal action; preemergence treatment in the greenhouse

| Active ingredient | kg/ha | Test plants and % damage | | | | |
|---|---|---|---|---|---|---|
| | | Oryza sativa | Zea mays | Centaurea cyan. | Sida spinosa | Solanum nigrum |
| prior art | | | | | | |

0 = no damage
100 = non-emergence or plants destroyed

TABLE 3

Selective herbicidal action; postemergence treatment in the greenhouse

| Active ingredient | kg/ha | Test plants and % damage | | | | | | | |
|---|---|---|---|---|---|---|---|---|---|
| | | Oryza Sativa | Zea mays | Avena fatua | Chenopod. spp. | Datura stramon. | Euphorb. genic | Matric cham. | Solan. nigr. |
| No. 1 | 1.0 | 8 | 10 | 82 | 83 | 100 | 98 | 80 | 100 |
| A prior art | 1.0 | 32 | 25 | 62 | 55 | 80 | 20 | 60 | 77 |

0 = no damage
100 = non-emergence or plants destroyed

We claim:

1. A 6H-1,2,4,6-thiatriazine-1,1-dioxide of the formula

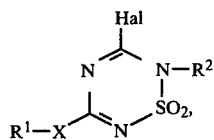

where $R^1$ is an alkyl, alkenyl or alkynyl radical of up to 10 carbon atoms, a cycloalkyl radical of 3 to 7 carbon atoms, a branched, saturated or unsaturated alkyl, alkenyl or alkynyl radical of 3 to 10 carbon atoms, a halogen-, alkoxy- or alkylmercapto-substituted straight-chain or branched alkyl, alkenyl or alkynyl radical of 2 to 10 carbon atoms, a cycloalkoxy-substituted alkyl, alkenyl or alkynyl radical of 4 to 10 carbon atoms, unsubstituted or halogen-, lower alkyl- or lower alkoxy-substituted phenyl, or unsubstituted or halogen-substituted benzyl, $R^2$ is hydrogen, an alkyl radical of 1 to 10 carbon atoms, a cycloalkyl radical of 3 to 7 carbon atoms, a branched alkyl radical of 3 to 10 carbon atoms or halogen- or alkoxy-substituted alkyl of 2 to 10 carbon atoms, X is oxygen, sulfur, sulfinyl or sulfonyl and Hal is halogen.

2. A 6H-1,2,4,6-thiatriazine-1,1-dioxide of claim 1 wherein $R^1$ and $R^2$ are selected from the group consisting of methyl, ethyl, propyl, isopropyl, cyclopropyl, butyl, isobutyl, sec.-butyl, tert.-butyl, 1-pentyl, cyclopentyl, hexyl, cyclohexyl, 3-pentyl, 1,2-dimethylpropyl, 1,3-dimethylbutyl, 2-chloroethyl, 2-chloropropyl, 3-chloropropyl, 2-chloroisopropyl, 1-chloromethylpropyl, 1-ethyl-2-methylpropyl, 1,2,2-trimethylpropyl, 1,2-dimethylhexyl, 1-cyclohexylethyl, 2-chlorobut-3-yl, 2-chloro-2-methylpropyl, 2-fluorobut-3-yl, 2-fluoro-2-methylpropyl, 2-fluoroisopropyl, tert.-amyl, chloro-tert.-butyl, 2,2,2-trifluoroethyl, methoxyethyl, ethoxyethyl, 3-methoxypropyl, methoxyisopropyl, 3-methoxybutyl, 1-methoxy-but-2-yl, ethoxy-tert.-butyl, methoxy-tert.-butyl, 2-methoxy-butyl and 4-methoxybutyl and wherein $R^1$ can further be allyl, methallyl, crotyl, 2-ethyl-hex-2-en-1-yl, hex-5-en-1-yl, 2-methyl-but-2-en-1-yl, 2-methyl-but-1-en-3-yl, but-1-yn-3-yl, but-2-yn-1-yl, but-1-en-3-yl, propargyl, 2-methyl-but-1-en-4-yl, 2-methyl-but-2-en-4-yl, 3-methyl-but-1-en-3-yl, methylmercaptoethyl, ethylmercaptoethyl, 3-methylmercapto-propyl, 3-methylmercapto-butyl, 1-methylmercapto-but-2-yl, methylmercapto-tert.-butyl, 2-methylmercapto-butyl, cyclohexoxy-ethyl, benzyl, 2,6-dichlorobenzyl, 2-chloro-6-fluorobenzyl, 2,6-difluorobenzyl, phenyl, 4-chlorophenyl, 3,4-dichlorophenyl, 4-tert.-butylphenyl, 4-methoxy-3-chlorophenyl, 4-methoxyphenyl, 2-methylphenyl and 2-methyl-4-chlorophenyl and wherein Hal is fluorine, chlorine, bromine or iodine.

* * * * *